(12) United States Patent
Chandler

(10) Patent No.: US 11,255,842 B2
(45) Date of Patent: Feb. 22, 2022

(54) METHODS FOR DETECTING NEUTRALIZING ANTIBODIES TO PARATHYROID HORMONE (PTH) AND PARATHYROID HORMONE-RELATED PEPTIDE (PTHRP) ANALOG

(71) Applicant: Radius Health, Inc., Boston, MA (US)

(72) Inventor: Heidi K. Chandler, Boxborough, MA (US)

(73) Assignee: Radius Health, Inc., Boston, MA (US)

( * ) Notice: Subject to any disclaimer, the term of this patent is extended or adjusted under 35 U.S.C. 154(b) by 0 days.

(21) Appl. No.: 17/369,163

(22) Filed: Jul. 7, 2021

(65) Prior Publication Data

US 2021/0389300 A1 Dec. 16, 2021

Related U.S. Application Data

(63) Continuation of application No. PCT/IB2020/050200, filed on Jan. 10, 2020.

(60) Provisional application No. 62/791,267, filed on Jan. 11, 2019.

(51) Int. Cl.
*G01N 33/50* (2006.01)

(52) U.S. Cl.
CPC ... *G01N 33/5032* (2013.01); *G01N 2333/635* (2013.01)

(58) Field of Classification Search
CPC ..................... G01N 33/5032; G01N 2333/635
See application file for complete search history.

(56) References Cited

FOREIGN PATENT DOCUMENTS

WO WO-2014011416 A2 1/2014

OTHER PUBLICATIONS

Hohenstein, et al., "Development and validation of a novel cell-based assay for potency determination of human parathyroid hormone (PTH)," Publ. Jun. 10, 2014, Journal of Pharmaceutical and Biomedical Analysis, vol. 98, pp. 345-350. (Year: 2014).*
Hohenstein, Axel et al., "Development and validation of a novel cell-based assay for potency determination of human parathyroid hormone (PTH)", Journal of Pharmaceutical and Biochemical Analysis, vol. 98, pp. 345-350 (Sep. 1, 2014).
(Continued)

*Primary Examiner* — Jennifer Wecker
*Assistant Examiner* — Michael Paul Shimek
(74) *Attorney, Agent, or Firm* — Womble Bond Dickinson (Us) LLP; Danielle L. Herritt; Scott R. Breining (57) ABSTRACT

The present disclosure is directed to methods (e.g., in vitro methods) for detecting the presence of neutralizing antibodies to PTH or PTHrP analog in a sample. The in vitro method comprises the steps of obtaining a sample from a subject; contacting the sample with a cell; measuring cyclic adenosine monophosphate (cAMP) levels; and detecting the presence of neutralizing antibodies when cAMP levels are reduced relative to a negative control sample without neutralizing antibodies. An in vitro method of detecting the presence of neutralizing antibodies in a sample from a subject treated with Abaloparatide, is also provided. Further provided herein is a kit for carrying out the methods described herein comprising components required to carry out the obtaining, contacting, measuring and detecting steps and instructions for use.

20 Claims, 2 Drawing Sheets

(56) References Cited

OTHER PUBLICATIONS

Leder, Benjamin Z. et al., "Effects of Abaloparatide, a Human Parathyroid Hormone-Related Peptide Analog, on Bone Mineral Density in Postmenopausal Women with Osteoporosis", Journal of Clinical Endocrinology and Metabolism, vol. 100, No. 2, pp. 697-706 (Feb. 1, 2015).
International Search Report and Written Opinion for Application No. PCT/IB2020/050200, dated Apr. 28, 2020, 10 pages.

* cited by examiner

METHODS FOR DETECTING NEUTRALIZING ANTIBODIES TO PARATHYROID HORMONE (PTH) AND PARATHYROID HORMONE-RELATED PEPTIDE (PTHRP) ANALOG

RELATED APPLICATIONS

This application is a continuation of International Application No. PCT/IB2020/050200, filed Jan. 10, 2020, and claims the benefit of priority to U.S. Provisional Application No. 62/791,267, filed on Jan. 11, 2019, the entire contents of each of which is incorporated herein by reference for all purposes.

BACKGROUND

Despite the benefits, immunogenicity can arise from protein therapeutics such as Abaloparatide. Abaloparatide is a parathyroid hormone-related peptide (PTHrP) (1-34) analog which acts as a PTH1 receptor (PTH1R) agonist. Activation of the PTH1R activates the cyclic adenosine monophosphate (cAMP) signaling pathway in target cells, which results in increases in bone mineral density and bone mineral content. TYMLOS® (Abaloparatide) Injection Product Label (Apr. 28, 2017).

Of the patients receiving Abaloparatide for 18 months, 49% developed anti-Abaloparatide antibodies, 68% of which developed neutralizing antibodies to Abaloparatide. Of these patients tested for cross-reactivity, 2.3% and 0% developed cross-reactivity to PTHrP and parathyroid hormone (PTH), respectively. Of the patients that developed cross-reactivity to PTHrP, 43% developed neutralizing antibodies to PTHrP.

Detection of antibodies, such as neutralizing antibodies, can also be used to monitor the development of potential immunogenicity in patients treated with PTH and/or PTHrP analog. However, current detection methods suffer from a number of drawbacks including the level of sensitivity, the level of specificity as well as the lengthy duration of the assays. Sensitive and specific assays are needed to detect and monitor the presence of neutralizing antibodies to PTH and PTHrP.

SUMMARY

The present disclosure is directed to methods (e.g., in vitro cell-based assays) for the detection of neutralizing antibodies (NAb) to PTH or PTHrP analog.

A first aspect provides an in vitro method for detecting the presence of neutralizing antibodies to PTH or PTHrP in a sample that includes the steps of obtaining the sample from a subject; contacting the sample with a population of cells or a cell and a predetermined amount of PTH or PTHrP, wherein the cell or cells comprise a receptor for PTH or PTHrP; measuring cyclic adenosine monophosphate (cAMP) levels; and detecting the presence of neutralizing antibodies when cAMP levels are reduced relative to a negative control sample without neutralizing antibodies. In some embodiments, the contacting step comprises incubating the cell or cells with the serum sample. In certain embodiments, the method further comprises preincubation of the serum sample with a predetermined amount of PTH or PTHrP prior to the contacting step. In a particular embodiment, the preincubation is for a period of at least 30 minutes. In certain embodiments, the predetermined amount of PTH or PTHrP is at least 100, 200, 300, 400, or 500 pg/mL. In a specific embodiment, the predetermined amount of PTH is about 500 pg/mL. In another specific embodiment, the predetermined amount of PTHrP analog is about 600 pg/mL.

In certain embodiments, the method further comprises incubation of the cell or cells with a cell permeable cAMP-specific phosphodiesterase inhibitor prior to the contacting step. In a particular embodiment, the cAMP-specific phosphodiesterase inhibitor is 4-(3-Butoxy-4-methoxybenzyl)-2-imidazolidinone.

In some embodiments, the measuring step is performed by a competitive immunoassay. In certain embodiments, the competitive immunoassay is an electrochemiluminescent detection method. In certain embodiments, the cell or cells are lysed prior to the measuring step. In certain embodiments, the measuring of cAMP levels is performed using the Mesoscale Discovery Multi-Array 96-well cAMP Plate.

In some embodiments, the cell or population of cells are rat epithelial cell line UMR-106. In certain embodiments, the method further comprises serum-starving the UMR-106 cell or cells for a period of time prior to the contacting step. In certain embodiments, the period of time ranges from about 4 hours to about 48 hours, about 4 hours to about 24 hours, about 4 hours to about 16 hours, about 4 hours to about 12 hours, or about 6 hours to about 12 hours.

In some embodiments, the sample is a human sample. In certain embodiments, the human sample is a human serum sample. In certain embodiments, the sample is from the subject treated with a PTHrP analog. In a specific embodiment, the PTHrP analog is Abaloparatide. In another specific embodiment, the PTHrP analog is Teriparatide.

Another aspect provides a method of detecting the presence of neutralizing antibodies after Abaloparatide treatment, the method comprising the steps of: obtaining a serum sample from a subject treated with Abaloparatide; contacting the serum sample with a cell or population of cells, wherein the cell or cells comprise a receptor for PTH or PTHrP; measuring cyclic adenosine monophosphate (cAMP) levels; and detecting the presence of neutralizing antibodies when cAMP levels are reduced relative to a negative control sample without neutralizing antibodies. In certain embodiments, the method further comprises discontinuing treatment with Abaloparatide when neutralizing antibodies are detected in the serum sample.

In yet another aspect, the disclosure provides a kit for carrying out the methods described herein comprising components required to carry out the obtaining, contacting, measuring and detecting steps and instructions for use.

DETAILED DESCRIPTION

A. Definitions

The term "antibody" refers to a full antibody, e.g., an antibody comprising two heavy chains and two light chains, or to an antigen-binding fragment of a full antibody, and encompasses any polypeptide comprising an antigen-binding site (e.g., site binding to PTH or PTHrP analog Abaloparatide) regardless of the source, species of origin, method of production, and characteristics. As a non-limiting example, the term "antibody" includes human, orangutan, mouse, rat, goat, sheep, and chicken antibodies. The term includes, but is not limited to, polyclonal, monoclonal, mono-specific, poly-specific, non-specific, humanized, single-chain, chimeric, synthetic, recombinant, hybrid, mutated, and CDR-grafted antibodies. The term "antibody" also includes, but is not limited to, antibody fragments produced by digestion with various proteases, those produced by chemical cleavage and/or chemical dissociation, and those produced recombinantly. Among these fragments are Fab, Fab', F(ab')Zf Fv, scFv, Fd, dAb, and other antibody fragments that retain the antigen-binding function. The antibody or fragment thereof may be any of the known antibody isotypes and their conformations, for example, IgA, IgG, IgD, IgE, IgM monomers, IgA dimers, IgA trimers, or IgM pentamers.

The term "neutralizing antibody", as described herein refers to any antibody or fragment thereof capable of binding to and interfering with at least one biological activity of PTH or PTHrP analog for which the antibody is specific. The neutralizing antibody may inhibit (i.e., eliminate or reduce) one or more activities of PTH or PTHrP analog without inhibiting other activities of PTH or PTHrP.

The terms "cut point" or "assay cut point", refer to the level of response (e.g., reduction of cAMP levels or reduced induction of cAMP by PTH or PTHrP) at or below which a sample is defined to be negative and above which it is defined to be positive for neutralizing activity towards PTH or PTHrP analog. The cut point can be a fixed cut point or a variable one to account for the variable nature of cell based assays. Cut point is typically tied to a statistical measure of a control sample (e.g., negative control sample with no neutralizing antibodies for PTH or PTHrP analog). For example, the statistical measure can be a standard deviation, a standard error, a mean, a median, a median absolute deviation, a fit parameter, or the like.

"Specificity", as determined in the assays described herein, establishes that only the positive control shows a neutralizing response of decreased cAMP induction and any other non-specific immunoglobulin doesn't show this response. "Selectivity" is the ability of the assay described herein to differentiate and detect the specific decrease in either cAMP levels or cAMP induction in the presence of other components present in the sample (interfering substances). Selectivity can vary between test samples due to the heterogeneous and polymorphic nature of samples.

The term "subject" refers to an animal. In some embodiments, the animal is a mammal, including but not limited to a human, a bovine, or a rodent. In other embodiments, the mammal is a human.

B. Assays for the Measurement of Neutralizing Antibodies Against PTH and PTHrP Analog The disclosure is based on the development of specific and selective assays for the measurement of neutralizing antibodies against PTH and/or PTHrP analog. Neutralizing antibodies can be detected using various cell-based systems. In these cell-based assays, neutralizing antibodies inhibit the ability of the therapeutic agent to modulate a biological process in the target cell (e.g., induction of cAMP by PTH). Neutralizing antibodies can be detected using cell-based systems involving a biological functional readout, such as measuring levels or induction activity of a biomarker.

In an aspect, an in vitro method for detecting the presence of neutralizing antibodies to PTH or PTHrP in a sample is provided. The method includes: (i.) obtaining a sample from a subject (ii.) contacting the sample with a population of cells and an predetermined amount of PTH or PTHrP, wherein the cells comprise a receptor for PTH or PTHrP analog such as PTH1R; (iii.) measuring cyclic adenosine monophosphate (cAMP) levels; and (iv.) determining the presence of neutralizing antibodies when cAMP levels are reduced relative to a negative control sample without neutralizing antibodies.

In some embodiments, the samples of this disclosure may be any bodily fluid capable of containing neutralizing antibodies against PTH or PTHrP analogs such as Abaloparatide. Examples include, but are not limited to, blood, serum, lymph, plasma, synovial fluid, cerebrospinal fluid, lachrymal fluid, biopsy or tissue sample, cell suspension, saliva, oral fluid, mucus, amniotic fluid, colostrums, mammary gland secretions, urine, sweat and tissue culture medium.

In some embodiments, the disclosure provides a method for the detection of neutralizing antibodies by measuring cAMP level by a competitive immunoassay. In some embodiments, the competitive immunoassay is an electrochemiluminescent detection method.

For example, the competitive immunoassay to validate a cell-based assay in post-menopausal women for the detection of neutralizing antibodies (NAb) to the PTH or PTHrP analog may be carried out as follows. The human serum sample, which may or may not contain potentially neutralizing antibodies, is first preincubated with predetermined amounts of PTH or PTHrP analog for at least 30 minutes. Serum starved rat epithelial cell UMR 106 cells are harvested by trypsinization and resuspended at 106 cells/mL in assay medium containing 133.5 uM of 4-(3-Butoxy-4-methoxybenzyl)-2-imidazolidinone, a cell-permeable cAMP-specific phosphodiesterase inhibitor. About forty microliters of the cell suspension are added to the cAMP assay plates that already have about twenty microliters of samples and/or controls. The cells in the cell suspension may or may not be lysed. If the cells are lysed, the cells may be lysed while still adhered to the culture plates. Lysis is carried out in presence of commonly known lysis buffers, preferably using lysis buffer while being incubated at room temperature for a time period of about 5 minutes to about 30 minutes, preferably about 10 minutes.

In some embodiments, the samples of this disclosure may be assayed at multiple dilutions to obtain an accurate quantitation of neutralizing activity present in the sample. In other embodiments, the samples of this disclosure may be assayed undiluted to obtain an accurate quantitation of neutralizing activity present in the sample. In some embodiments, the samples of this disclosure may also be diluted to avoid interference from non-specific background components of the samples. For example, proteins found at high concentrations in the serum may, in some circumstances, non-specifically interact with components of the assay and reduce the sensitivity of the assay. Sample dilution may reduce or eliminate non-specific binding and thereby increase the signal-to-noise ratio of the assay.

In some embodiments, the samples of this disclosure may be assayed at dilution factors such as, for example, 1:1, 1:2, 1:5, 1:10, 1:15, 1:20, 1:30, 1:40, 1:50, 1:60, 1:80, 1:100, 1:32, 1:640, 1:500, 1:1000, 1:1280, 1:2560 or 1:5000. In other embodiments, the samples of the disclosure may be assayed at a further serial dilution of the diluted sample.

After a minimum of 30 minutes at room temperature with shaking, TAG cAMP detection reagent (Mesoscale Delivery, MSD Multi-Array 96-well cAMP Kit) diluted 1:200 in MSD Lysis Buffer is added to the assay plates. Reagents were used as provided in kit and prepared as per manufacturer's instructions. Plates are incubated at room temperature for an additional 1 to 2 hours with shaking. One hundred microliters of 2×MSD Read Buffer T are then added to the plates and plates are read immediately on an MSD 6000 or S6000 Sector Imager.

The drug-spike assay involved treatment of the rat epithelial cell line UMR-106 in the presence of human serum which may or may not contain neutralizing antibodies (NAb), followed by measurement of the ability of the predetermined amount of PTH or PTHrP analog to induce cellular cyclic adenosine monophosphate (cAMP) by competitive immunoassay. In certain embodiments, the serum sample is preincubated with a predetermined amount of PTH or PTHrP analog prior to the contacting step. While not being bound by theory, any PTH or PTHrP analog neutralizing antibodies present in the sample will interact with and neutralize PTH or PTHrP analog and neutralize it during the preincubation step. Thus, when the mixture of the preincubated serum and PTH or PTHrP analog is incubated with the population of cells, neutralized PTH or PTHrP analog will not induce PTH1R receptor and hence will result in the reduction in the levels of cAMP.

In some embodiments, the predetermined amount or concentration of PTH or PTHrP analog is at least 100, 200, 300, 400, or 500 pg/mL. In some embodiments, the predetermined amount of PTH is about 500 pg/mL. In some embodiments, the predetermined amount of PTHrP analog is about 600 pg/mL. In some embodiments, the samples were evaluated in the presence of a final concentration of 500 pg/mL of PTH or PTHrP analog. In other embodiments, the samples were evaluated in the presence of a final concentration of at least 100 pg/mL, at least 200 pg/mL, at least 300 pg/mL, at least 400 pg/mL, at least 500 pg/mL or at least 600 pg/mL of PTH or PTHrP analog. In some embodiments, the samples were evaluated in the presence of a final concentration of 500 pg/mL of PTH. In some embodiments, the samples were evaluated in the presence of a final concentration of 600 pg/mL of PTHrP analog.

Figure 1:
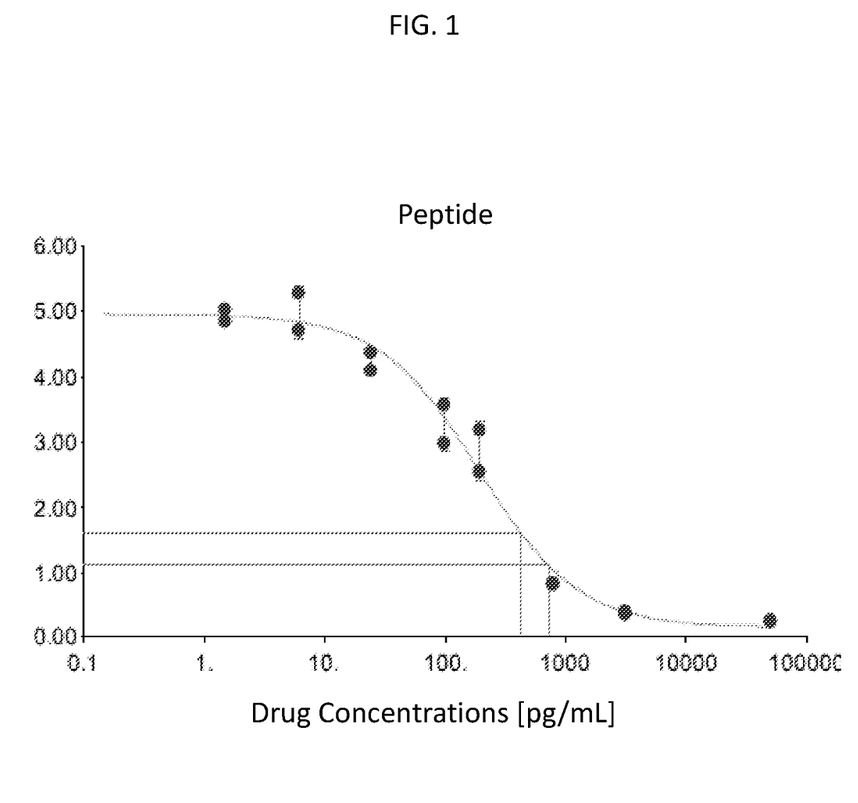
FIG. 1 is a graph depicting exemplary 4-parameter logistic fit of PTH Peptide Dilutions in 25% PHS.
Figure 2:
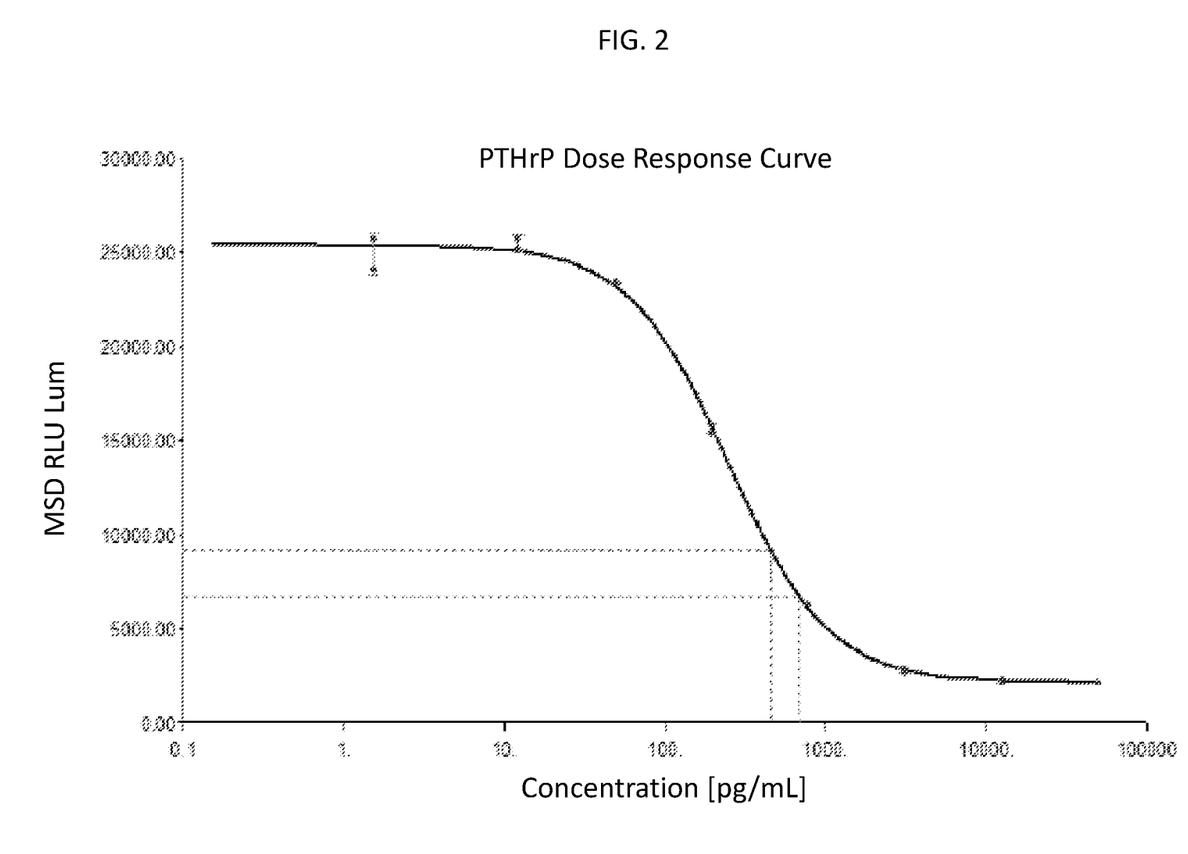
FIG. 2 is a graph depicting an exemplary PTHrP analog Dose Response Curve.

FIGS. 1 and 2 show a curve fit from a single qualification run and is representative of the PTH and PTHrP dose response observed, respectively. The dotted lines indicate the EC20 and EC30 of the PTH and PTHrP responses in the presence of 25% pooled human serum as interpolated from the curve fit, respectively. As represented in FIGS. 1 and 2 the dose response curve and neutralization of PTH or PTHrP induced cAMP induction represents the robust endpoint.

The cAMP levels, can be measured using any method known in the art. For example, the cAMP can be measured using an ELISA assay to detect PTH1R levels or activity. In some embodiments, the measuring cAMP level is performed using the Mesoscale Discovery Multi-Array 96-well cAMP Plate.

The present methods can determine if PTH or PTHrP analog neutralizing antibodies are or are not present in the serum sample in an amount sufficient to significantly neutralize PTH or PTHrP analog. In certain embodiments, an assay cut point can be calculated to determine when PTH or PTHrP analog neutralizing antibodies are present in the sample. The method may further comprise determining an assay cut point based on a negative control of pooled human serum, correlating the assay cut point with the presence of neutralizing antibodies, and comparing the amount of cAMP reduction in the population of cells to the assay cut point. For example, when a measured amount of cAMP reduction in the sample is less than of the assay cut point, then the serum sample does not contain appreciable quantities of the neutralizing antibodies and when a detected amount of cAMP reduction in the sample is higher than of the assay cut point, then the serum sample contains appreciable quantities of the neutralizing antibodies.

In some embodiments, the responses induced by positive and negative control samples are determined to ensure that the assay is functioning properly. Negative controls are typically pooled human serum samples from a subject that has not been exposed to the PTH and/or PTHrP analogs. In some instances, the negative control samples may be pooled serum samples from untreated subjects.

In some embodiments, the positive controls include serum samples from subjects treated with a PTH and/or PTHrP analogs. In other embodiments, the control includes serum samples from subjects spiked with a surrogate neutralizing antibody (SPC). In some embodiments, the serum samples are pooled. In some embodiments, the serum samples are pooled from individual disease state serum samples from post-menopausal women. In other embodiments, the serum is human serum obtained from individual disease state serum samples from post-menopausal women. Additional positive controls may include frozen samples of pooled human serum with different dilutions of SPC, for example, SPC dilutions of 1:120, 1:240, 1:500, and 1:800 for the high positive control (HPC), mid positive control (MPC), low positive control-1 (LPC1) and low positive control-2 (PC2), respectively.

In some embodiments, the cell or population of cells of this disclosure may be any cells that express PTH1R and allows the induction of cAMP signaling, resulting in activation of the PTH1R and the cAMP signaling pathway. In some embodiments, the assays of this disclosure may use one cell or a population of cells. In some embodiments, the cell or population of cells is rat epithelial cell line UMR-106.

Cells are grown at any density appropriate for normal cell growth when used in the assays of this disclosure. The number of cells used to achieve an appropriate density is determined in part by the size and surface area of the plate used in the assay. Cells may be used in the assay at any density. In some embodiments, the cells may be used in the assays at the following cell densities: at least 10% confluent, at least 25% confluent, at least 50% confluent, at least 80% confluent, at least 90o confluent, or at least 99% confluent.

In certain embodiments, the method comprises serum starving the UMR-106 cell or cells for a period of time prior to contacting them with the sample during the contacting step. The cells may be serum starved for a period of time ranging from about 4 hours to about 48 hours, about 4 hours to about 24 hours, about 4 hours to about 16 hours, about 4 hours to about 12 hours, or about 6 hours to about 12 hours.

In some embodiments, the sample is a human sample. In some embodiments, the sample is a human serum sample.

In some embodiments, the sample is from the subject treated with a PTHrP analog. In some embodiments, the PTHrP analog is Abaloparatide. In other embodiments, the PTHrP analog is Teriparatide.

Detection of antibodies, such as neutralizing antibodies, can also be used to monitor the development of potential immunogenicity in patients treated with PTH or PTHrP analog. For example, neutralizing antibodies in patients treated with PTHrP analog for osteoporosis could be important in detecting and minimizing the effects of adverse reactions, optimizing drug dosage and efficacy of treatment. In an aspect, described herein is a method for detecting the presence of neutralizing antibodies after Abaloparatide treatment. The method comprises obtaining a sample (e.g., pooled or individual human serum sample) from a subject treated with Abaloparatide, contacting the sample with a cell or population of cells, wherein the cells comprise a receptor for PTH or PTHrP, measuring cyclic adenosine monophosphate (cAMP) levels, and detecting the presence of neutralizing antibodies when cAMP levels are reduced relative to a negative control sample without neutralizing antibodies.

The assay described herein provides a convenient and reliable alternative to actual clinical trials that may quickly ascertain whether adverse immunogeneic events are likely based on potential anti-PTH or anti-PTHrP analog antibody production. In some embodiments, the methods of the disclosure can be used to diagnose the onset of adverse immunogenic events post-Abaloparatide treatment. In some embodiments of the method, the treatment with Abaloparatide is discontinued when neutralizing antibodies are detected in the serum sample. In other embodiments, when the serum sample does not contain neutralizing antibodies, the method further comprises continuing the treatment of the subject with Abaloparatide. In yet another embodiments of the method, the dosage of Abaloparatide is varied (decreased or increased) when neutralizing antibodies are detected in the serum sample.

In some embodiments, the samples may also have tested positive in a different primary neutralizing antibody assay and are now being subjected to the assay as a confirmatory assay for the presence of neutralizing antibodies. In some other embodiments, the samples are prescreened with an immunoassay, such as an ELISA assay. In yet other embodiments, the samples are prescreened with a cell-based assay, such as, for example, the downregulation of a reporter gene. The reporter gene may be the luciferase gene. The luciferase gene may be linked to a promoter of a gene encoding PTH1R.

In some embodiments, antibody concentrations of anti-PTH or anti-PTHrP analog are determined any one of or combination of immunodiagnostic methods based on detection of complex antigen-antibody, including, for example, enzyme-linked immunosorbent assay (ELISA), receptor binding assay, radio-immunoprecipitation, biosensor-based assay, immunofluorescence, Western blot, immunodiffusion, and immunoelectrophoresis. In a particular embodiment, antibody concentrations of anti-PTH or anti-PTHrP analog are determined by ELISA using polyclonal or monoclonal antibodies of anti-PTH or anti-PTHrP analog, as standards.

C. Kits

The reagents described herein may be provided in kit format. A kit may include, for instance, some or all of the components necessary to carry out the assays described herein. For instance, the kit may comprise control compositions (e.g., control human serum samples without neutralizing antibodies against PTH or PTHrP analog), test cells (e.g., UMR-106 cells affixed to a solid support, and/or frozen), buffers, labeling reagents (e.g., labeled antibodies such as goat anti-mouse IgG biotin, streptavidin-HRP conjugates, allophycocyanin, B-phycoerythrin, R-phycoerythrin, peroxidase, and/or other detectable labels), instructions to carry out the assay and any other necessary or useful components. The components of the kit may be provided in any suitable form, including frozen, lyophilized, or in a pharmaceutically acceptable buffer such as TBS or PBS. The kit may also include a solid support containing one or more test cells (e.g., microorganisms) in any suitable form. The kits may also include other reagents and/or instructions for carrying out assays such as, for example, competitive inhibition assay, MSD cAMP assay, flow cytometric analysis, ELISA, immunoblotting (e.g., western blot), in situ detection, immunocytochemistry, immunohistochemistry, and/or visualization of data. Kits may also include components such as containers (e.g., tubes) and/or slides pre-formatted to containing control samples and/or reagents with additional space (e.g., tubes, slides and/or space on a slide) for experimental samples. The kit may also comprise one or both of an apparatus for handling and/or storing the sample obtained from the individual and an apparatus for obtaining the sample from the subject (i.e., a needle, lancet, and collection tube or vessel). Other embodiments are also provided as would be understood by one of ordinary skill in the art.

EXAMPLES

Example 1. Anti-PTH Assay Validation and Calibration

A study was undertaken to validate a cell-based assay in post-menopausal women for the detection of neutralizing antibodies (NAb) to the PTH peptide. The assay involved treatment of the rat epithelial cell line UMR-106 in the presence of human serum which may or may not contain neutralizing antibodies (NAb), followed by measurement of the ability of PTH to induce cellular cyclic adenosine monophosphate (cAMP) by competitive immunoassay. The detection of cAMP was performed using a competitive electrochemiluminescent assay, where neutralizing antibodies to PTH resulted in decreased induction of cAMP by PTH and an increased assay signal.

Materials

Reagents used for PTH assay validation are shown in Table 1 and Table 2, below.

TABLE 1

| Reagent | Source | Batch/Lot Number |
|---|---|---|
| UMR-106 Rat Osteosarcoma; Working Cell Bank (WCB); Passage 4* | ATCCP/N CRL-1661, Lot#61465075 | RP18Jun15SW01 |
| Parathyroid Hormone Peptide(PTH)(1-34)(Human) | Phoenix Pharmaceuticals P/N 055-08 | 055-08430926 |
| Anti-PTH Antibody (SPC)(1-34)(Human specificity) 29.84 µg/mL** | Phoenix Pharmaceuticals G-055-08 | 01553-4 |
| High antibody positive control (4X HPC), 1:175 Dilution, 170.1 ng/mL | Prepared from Anti-PTH Antibody at BioAgilytix Labs | RP23May16JNN02 |
| Mid antibody positive control (4X MPC), 1:250 Dilution, 119.4 ng/mL | Prepared from Anti-PTH Antibody at BioAgilytix Labs | RP23May16JNN03 |
| Low antibody positive control (4X LPC1), 1:300 Dilution, 99.5 ng/mL | Prepared from Anti-PTH Antibody at BioAgilytix Labs | RP23May16JNN04 |
| Low antibody positive control (4X LPC2), 1:400 Dilution, 74.6 ng/mL | Prepared from Anti-PTH Antibody at BioAgilytix Labs | RP23May16JNN05 |
| MSD Multi-Array 96-well cAMP Plate | MesoScale Discovery (MSD) Kit component of P/N K150FDD | Z0000447 |

*Note that the passage numbers on the WCB vials were labeled incorrectly and should read P4 as "passage at thaw."
**Concentration determined by quantitative ELISA

TABLE 2

| Description | Source/Vendor | Catalog Number |
|---|---|---|
| Dulbecco's Phosphate Buffered Saline (DPBS) | Gibco/Life Technologies | 14190 |
| TrypLE Express | Gibco/Life Technologies | 12604 |
| 0.4% Trypan Blue Solution | Gibco/Life Technologies | 15250 |
| Dulbecco's Modified Eagle Medium (DMEM), 1X, high-glucose | Gibco/Life Technologies | 1195-065 |
| Fetal Bovine Serum (FBS) | Gibco/Life Technologies | 16000 |
| Penicillin-Streptomycin (Pen/Strep): 10,000 units/mL Pen; 10,000 mg/mL Strep | Gibco/Life Technologies | 15140-122 |
| 200 mM 1-glutamine )L-glut) | Gibco/Life Technologies | 25030-081 |
| Phenol Red-Free DMEM, 1X, high-glucose | Gibco/Life Technologies | 21063 |
| 30% Bovine Serum Albumin (BSA) | Sigma | A9576 |
| 50 mg Ro 20-1724 (M.W. 278.35) cAMP-specific phosphodiesterase inhibitor | R&D Systems/Tocris | 0415 |
| Dimethyl Sulfoxide (DMSO) | Sigma | D2438 |
| Tissue Culture Flasks (75 cm$^2$ with vented cap) | Corning | 430641 |
| Sterile 96-deep well Plate with lid | MP Biomedicals | 76-223-05 |
| MSD Multi-Array 96-well cAMP Kit components (not including plates_ TAG Labeled cAMP Read Buffer Y, with surfactant (4X) cAMP Lysis Buffer Blocker A | MesoScale Discovery (MSD) | R31AE-3 R92TC-2 R60AE-1 R93BA-4 |

To generate controls, pooled human serum (PHS), pooled from individual disease state serum samples from post-menopausal women (placebo controls); and individual disease state serum samples from post-menopausal women (placebo controls) were sourced from a clinical study.

Frozen Controls Included:
Frozen Negative control (NC)=Pooled Human Serum (PHS)
Frozen 4× high positive control (4×HPC)=Human serum pool spiked with 1:175 dilution of surrogate antibody positive control (SPC)
Frozen 4× mid positive control (4×MPC)=Human serum pool spiked with 1:250 dilution of SPC
Frozen 4× low positive control 1 (4×LPC1)=human serum pool spiked with 1:300 dilution of SPC
Frozen 4× low positive control 2 (4×LPC2)=human serum pool spiked with 1:400 dilution of SPC Each frozen control is diluted 1:4 for final assay SPC dilutions of 1:700, 1:1000, 1:1200 and 1:1600 for the high positive control (HPC), mid positive control (MPC), low positive control-1 (LPC1) and low positive control-2 (PC2), respectively.

Methods

UMR-106 cells are maintained in growth medium (UMR-GM, Dulbecco's Modified Eagle's Medium (DMEM) containing 10% Fetal Bovine Serum, 1% Pen-Strep (10 k units Penicillin—10 k ug/mL Streptomycin) and 1% L-glutamine) in 75-150 cm$^2$ tissue culture flasks until ready for use. Cells are split at a ratio between 1:4 and 1:20 when growth reaches ≥70% confluence for routing culture maintenance. Prior to initiating an assay, cells are plated in sub-culturing flasks (25 cm$^2$ to 150 cm$^2$) at a density of 10$^6$ cells/5 cm$^2$ (example 5e6 cells for T-75). The following day, flasks are starved with assay medium (UMR-Am, Phenol Red-Free DMEM, containing 1% Bovine Serum Albumin). The following day validation samples and antibody controls are pre-incubated with PTH peptide for a minimum of 30 minutes. The validation samples and controls are adjusted such that the final assay concentration of serum is equal to the assay minimum required dilution of 1:4. Twenty microliters of samples and/or controls are placed on a MSD cAMP assay plate. The starved UMR-106 cells are harvested by trypsinization and resuspended at 106 cells/mL in assay medium containing 133.5 uM of 4-(3-Butoxy-4-methoxybenzyl)-2-imidazolidinone, a cell-permeable cAMP-specific phosphodiesterase inhibitor (RO 20-1724, MW 278.35, R&D Systems/Tocris Catalog 0415). Forty microliters of the cell suspension are added to the cAMP assay plate. After a minimum of 30 minutes at room temperature with shaking, TAG cAMP detection reagent (Mesoscale Delivery, MSD Multi-Array 96-well cAMP Kit) diluted 1:200 in MSD Lysis Buffer is added to the assay plates. Plates are incubated at room temperature for an additional 1 to 2 hours with shaking. One hundred microliters of 2×MSD Read Buffer T are then added to the plates and plates are read immediately on an MSD 6000 or 56000 Sector Imager.

Results

PTH Drug Concentration

Relative light units (RLU) were read from assay plates on a Meso Scale Discovery (MSD) Sector 6000 electrochemiluminescent reader. Data were exported from the MSD database to permit further analysis. Calculations for establishing the assay cut point, including removal of outliers, were performed in JMP® software v12.01 (SAS, Cary, N.C.). Outlier determination proceeded stepwise. During stepwise outlier discrimination, the standard configuration of the JMP whisker and box plot was used to declare outliers. Specifically, replicates outside of whiskers (the interquartile range of the replicates (IQR) plus or minus 1.5 times the IQR) were determined to be outliers.

The assay cut point was established using 64 individual diseased-state placebo control serum samples provided by the sponsor. Samples were run in groups of 32, as singlets, three times within a total of six runs. The six runs were performed by three analysts over five days and produced 192 data points. A minimum of eight replicates of the negative control (NC) was included on each plate. All data points were normalized as specified above.

The following equation was applied:

$$\text{Normalized Value } (NormRLU) = \frac{RLU \text{ of Sample}}{\text{Mean } RLU \text{ of Negative Control}}$$

$$\text{Standard Deviation: } \sigma = \sqrt{\frac{\sum (x_i - \mu)^2}{n}}$$

$$\% \ CV = \frac{\text{Standard deviation of individual measurements}}{\text{Mean of individual measurements}} \times 100$$

$$\% \text{ Recovery} = \frac{\text{Observed}}{\text{Reference}} \times 100$$

where % CV is percent coefficient of variance and RLU is the Relative Light Units A drug final assay concentration of 500 pg/mL was established during the development and qualification of the assay in human serum and was obtained by spiking into the assay at a 12× concentration of 6 ng/mL. FIG. 1 shows a curve fit from a single qualification run and is representative of additional runs performed during qualification. The dotted lines indicate the EC20 and EC30 of the PTH response in the presence of 25% pooled human serum as interpolated from the curve fit. The rounded concentrations interpolated were 436 and 728 pg/mL, respectively for the EC30 and the EC20.

Statistical Method

All statistical analyses were completed using JMP Statistical Discovery Software (Version 12.01; SAS Institute, Inc., Cary, N.C., USA)). Statistical methods used for the analyses are consistent with procedures recommended by Shankar et al., 2008.

The study design for unspiked samples was two groups of samples measured over three runs, for a total of six runs. The design allowed for evaluation of mean effect due to group. The design also allowed for the estimation of random variation attributable to samples nested in groups and run number.

A linear mixed effects analysis of variance (ANOVA) model was used to investigate systematic (fixed) and random sources of variation in reported count values for disease state samples with no inhibitor present. Statistical analyses were performed on normalized results per plate by dividing the mean response of the sample by the mean of the NC plate. Group was defined as fixed effects in the ANOVA model, with least squares means compared at the 0.05 significance level to assess systematic differences in the mean response among levels of these factors. Random effects were defined in the model for sample, and group was nested within run and the residual. Distribution of the sample best linear unbiased predictor (BLUP) values was then examined to identify samples as biological statistical outliers using the outlier box-plot in JMP. The distribution of ANOVA conditional residual values was evaluated to identify "analytic" statistical outliers using again the outlier box-plot procedure within JMP's distribution platform. All normalized result values for samples identified by this criterion were removed and the statistical analysis was repeated until no further outliers were identified.

The linear mixed effects ANOVA of the normalized values identified 25 values as outliers. Seven values were identified as 'analytic' outliers. Six samples were identified as a 'biologic' statistical outlier, which excluded 18 results (6 samples×3 runs=18). All statistical outliers were excluded from the cut point assessment leaving 167 values for analysis.

The linear mixed effects ANOVA of these data revealed no statistically significant difference between sample groups (p-value=0.2082). The difference between samples accounted for 14.6% of the total variability. Most of the variability in the method was associated with the analytical components (47.2% due to run and 38.2% due to residual variation).

Sensitivity

To evaluate sensitivity, an ultrahigh positive control sample was prepared by spiking the SPC [29.84 pg/mL] into 25% PHS at a 1:20 dilution. The 1:20 dilution was then serially diluted 2-fold, resulting in eight total dilutions of the SPC of 1:20, 1:40, 1:80, 1:160, 1:320, 1:640, 1:1280 and 1:2560; this corresponds to a concentration range of 1492 ng/mL to 12 ng/mL in neat matrix. The samples were evaluated at the 1:4 MRD and in the presence of a final concentration of 500 pg/mL of PTH. The sensitivity was determined from four independent runs as the lowest concentration of the antibody dilution curve that was consistently detected as positive (above the cut point) based on the mean normalized value. Assay sensitivity data are shown in Table 3.

TABLE 3

Antibody Sensitivity

| SPC Dilution | SPC Conc. ng/mL | Run #1 Mean NormRLU | Results | Run #2 Mean NormRLU | Results | Run #3 Mean NormR LU | Results | Run #8 Mean NormRLU | Results | Average All Runs Avg NormRLU | Results |
|---|---|---|---|---|---|---|---|---|---|---|---|
| 1:20 | 1492 | 8.488 | Positive | 4.337 | Positive | 4.886 | Positive | 8.234 | Positive | 6.486 | Positive |
| 1:40 | 746 | 8.629 | Positive | 4.006 | Positive | 4.747 | Positive | 8.259 | Positive | 6.410 | Positive |
| 1:80 | 373 | 8.464 | Positive | 4.080 | Positive | 4.528 | Positive | 8.137 | Positive | 6.302 | Positive |
| 1:160 | 187 | 7.560 | Positive | 3.094 | Positive | 4.116 | Positive | 5.506 | Positive | 5.069 | Positive |
| 1:320 | 93 | 3.416 | Positive | 2.071 | Positive | 2.657 | Positive | 3.761 | Positive | 2.976 | Positive |
| 1:640 | 47 | 1.982 | Positive | 1.452 | Positive | 1.828 | Positive | 2.235 | Positive | 2.874 | Positive |
| 1:1280 | 23 | 1.395 | Positive | 1.176 | Positive | 1.569 | Positive | 2.110 | Positive | 1.562 | Positive |
| 1:2560 | 12 | 1.335 | Positive | 0.919 | Positive | 1.247 | Positive | 1.816 | Positive | 1.329 | Positive |
| Cut Point | 1.234 | | | | | | | | | | |

Final Sensitivity was calculated based on the assay MRD of 4-fold.
Data presented are from Runs 1-3, 8.

The SPC concentration range evaluated only achieved negative scoring (below the cut point) in one of four independent runs (Run #2) for the individual data points and the four parameter logistic regression (4PL) fitted response. The three other runs remained positive (above the cut point) even at the lowest SPC concentration evaluated (12 ng/mL). As shown in Table 3, the normRLU for each SPC concentration were averaged across runs and compared to the assay cut point, and negative scoring was not achieved. Therefore, in three of four runs, and by averaging all four runs, the sensitivity of the assay is ≤12 ng/mL.

Specificity by Non-Specific Immunoglobulin

Specificity was assessed by evaluating the reactivity of commercial human IgG in the assay. Three human IgG concentrations 10, 1.0 and 0.1 µg/mL were spiked into neat human serum pool (PHS) and evaluated in the presence of a final concentration of 500 pg/mL PTH. All specificity samples were below the assay cut point of 1.234 and were considered negative. Both the 1.0 and 0.1 µg/mL samples were within the acceptance criteria of 30% of the negative control, the IgG 10 µg/mL was 60% (40% less than negative control); however, there was no impact as the sample tested negative in the assay and a negative result qualitatively demonstrates that the sample had no activity in the assay. The results are summarized in Table 4.

TABLE 4

Specificity Results

| Condition | Mean NormRLU | CV (%) | Result |
|---|---|---|---|
| IgG 10 µg/mL | 0.600 | 23.1 | Negative |
| IgG 1.0 µg/mL | 0.976 | 18.0 | Negative |
| IgG 0.1 µg/mL | 1.114 | 7.7 | Negative |
| Negative Control | 1.000 | 11.7 | Negative |

Data presented are from Run 4.

Specificity by Drug Tolerance

Increasing the PTH drug concentration resulted in a rapid decrease in signal in the presence of the SPC. Because the assay cut point was established by a cellular response that was dependent upon a fixed concentration of PTH, it is expected that the assay would have limited drug tolerance. To evaluate this limit, the HPC, LPC1 and LPC2 were treated with 750, 1000 or 2000 pg/mL of PTH and compared to samples treated with nominal PTH at 500 pg/mL in a single run.

The signal response decreased for each control with increased drug concentration for each level of controls, except for LPC2 1.5x, which has no impact on the interpretation of the results. The results are shown in Table 10. The controls remained positive in the presence of increasing concentrations of PTH up to 1000 pg/mL. The results are in Table 5.

TABLE 5

Drug Tolerance Results

| Sample Name | Drug Assay Concentration | Mean NormRLU | CV (%) | Result |
|---|---|---|---|---|
| Control HPC nominal Drug | 500 pg/mL | 4.106 | 14.4 | Positive |
| HPC 1.5x nominal Drug | 750 pg/mL | 3.755 | 13.7 | Positive |
| HPC 2x nominal Drug | 1000 pg/mL | 2.772 | 6.5 | Positive |
| HPC 4x nominal Drug | 2000 pg/mL | 1.008 | 3.9 | Negative |
| Control LPC1 nominal Drug | 500 pg/mL | 2.916 | 5.7 | Positive |

TABLE 5-continued

Drug Tolerance Results

| Sample Name | Drug Assay Concentration | Mean NormRLU | CV (%) | Result |
|---|---|---|---|---|
| LPC1 1.5x nominal Drug | 750 pg/mL | 2.707 | 1.0 | Positive |
| LPC1 2x nominal Drug | 1000 pg/mL | 1.918 | 17.4 | Positive |
| LPC1 4x nominal Drug | 2000 pg/mL | 0.856 | 10.2 | Negative |
| Control LPC2 nominal Drug | 500 pg/mL | 2.472 | 7.4 | Positive |
| LPC2 1.5x nominal Drug | 750 pg/mL | 2.652 | 20.4 | Positive |
| LPC2 2x nominal Drug | 1000 pg/mL | 1.611 | 11.0 | Positive |
| LPC2 4x nominal Drug | 2000 pg/mL | 0.870 | 4.0 | Negative |

Data presented are from Run 8

Selectivity

Selectivity was assessed with a total of 10 individual placebo human serum samples. Each sample was tested unspiked as well as spiked with the anti-PTH, SPC stock at the HPC and LPC1 dilution levels of 1:175 (170.1 ng/mL) and 1:300 (99.5 ng/mL), respectively, and evaluated in the assay with controls at the MRD of 1:4. Samples were positive for the NAb when spiked with concentrations of antibody equal to the level of the HPC and LPC1 (Table 11). One sample, Sample 5, was also positive unspiked with a normalized mean of 1.863. Reference controls (NC, HPC, LPC1 and LPC2) were run on each assay plate as assay controls.

Example 2. Anti-PTHrP Assay Validation and Calibration

A study was undertaken to validate a cell-based assay in post-menopausal women for the detection of neutralizing antibodies (NAb) to the PTHrP peptide. The assay involved treatment of the rat epithelial cell line UMR-106 in the presence of human serum which may or may not contain neutralizing antibodies (NAb), followed by measurement of the ability of PTHrP to induce cellular cyclic adenosine monophosphate (cAMP) by competitive immunoassay. The detection of cAMP was performed using a competitive electrochemiluminescent assay, where neutralizing antibodies to PTHrP resulted in decreased induction of cAMP by PTHrP and an increased assay signal.

Materials

Reagents used for PTH assay validation are shown in Table 6 and Table 7, below.

TABLE 6

| Reagent | Source | Batch/Lot Number |
|---|---|---|
| UMR-106 Rat Osteosarcoma; Working Cell Bank (WCB); Passage #4* | ATCCP/N CRL-1661, Lot#61465075 | RP18Jun15SW01 |
| Parathyroid Hormone Peptide(PTH)(1-34)(Human, Rat, Mouse) | Phoenix Pharmaceuticals P/N 056-04 | 431987 |
| Anti-PTH Antibody (SPC)(1-34)(Human, Rat, Mouse) 69.98 µg/mL** | Phoenix Pharmaceuticals H-056-04 | 01553-4 |
| High antibody positive control (4X HPC), 1:30 Dilution, 2.30 µg/mL | Prepared from Anti-PTH Antibody Lot 017360-1 at BioAgilytix Labs | RP17May16DLM01 |
| Mid antibody positive control (4X MPC), 1:60 Dilution, 1.15 µg/mL | Prepared from Anti-PTH Antibody Lot 017360-1 at BioAgilytix Labs | RP17May16DLM02 |
| Low antibody positive control (LPC1), 1:125 Dilution, 0.55 µg/mL | Prepared from Anti-PTH Antibody Lot 017360-1 at BioAgilytix Labs | RP17May16DLM03 |

TABLE 6-continued

| Reagent | Source | Batch/Lot Number |
|---|---|---|
| Low antibody positive control (LPC2), 1:200 Dilution, 0.34 µg/mL | Prepared from Anti-PTH Antibody Lot 017360-1 at BioAgilytix Labs | RP17May16DLM04 |
| MSD Multi-Array 96-well cAMP Plate | MesoScale Discovery (MSD) Kit component of P/N K150FDD | Z0000447 |

*Note that the passage numbers on the WCB vials were labeled incorrectly and should read P4 as "passage at thaw."
**Concentration determined by quantitative ELISA

TABLE 7

| Description | Source/Vendor | Catalog Number |
|---|---|---|
| Dulbecco's Phosphate Buffered Saline (DPBS) | Gibco/Life Technologies | 14190 |
| TrypLE Express | Gibco/Life Technologies | 12604 |
| 0.4% Trypan Blue Solution | Gibco/Life Technologies | 15250 |
| Dulbecco's Modified Eagle Medium (DMEM), 1X, high-glucose | Gibco/Life Technologies | 1195-065 |
| Fetal Bovine Serum (FBS) | Gibco/Life Technologies | 16000 |
| Penicillin-Streptomycin (Pen/Strep): 10,000 units/mL Pen; 10,000 mg/mL Strep | Gibco/Life Technologies | 15140-122 |
| 200 mM l-glutamine )L-glut) | Gibco/Life Technologies | 25030-081 |
| Phenol Red-Free DMEM, 1X, high-glucose | Gibco/Life Technologies | 21063 |
| 30% Bovine Serum Albumin (BSA) | Sigma | A9576 |
| 50 mg Ro 20-1724 (M.W. 278.35) cAMP-specific phosphodiesterase inhibitor | R&D Systems/Tocris | 0415 |
| Dimethyl Sulfoxide (DMSO) | Sigma | D2438 |
| Tissue Culture Flasks (75 cm² with vented cap) | Corning | 430641 |
| Sterile 96-deep well Plate with lid | MP Biomedicals | 76-223-05 |
| MSD Multi-Array 96-well cAMP Kit components (not including plates_ TAG Labeled cAMP Read Buffer Y, with surfactant (4X) cAMP Lysis Buffer Blocker A | MesoScale Discovery (MSD) | R31AE-3 R92TC-2 R60AE-1 R93BA-4 |

To generate controls, pooled human serum (PHS), pooled from individual disease state serum samples from post-menopausal women (placebo controls); and individual disease state serum samples from post-menopausal women (placebo controls).

Frozen controls included:
Frozen Negative control (NC)=Pooled Human Serum (PHS)
Frozen 4× high positive control (4×HPC)=Human serum pool spiked with 2.30 ug/mL of surrogate antibody positive control (SPC)
Frozen 4× mid positive control (4×MPC)=Human serum pool spiked with 1.15 ug/mL of SPC
Frozen 4× low positive control 1 (4×LPC1)=human serum pool spiked with 0.55 ug/mL of SPC
Frozen 4× low positive control 2 (4×LPC2)=human serum pool spiked with 0.34 ug/mL of SPC Each frozen control is diluted 1:4 for final assay SPC dilutions of 1:120, 1:240, 1:500, and 1:800 for the high positive control (HPC), mid positive control (MPC), low positive control-1 (LPC1) and low positive control-2 (PC2), respectively.

Methods

UMR-106 cells are maintained in growth medium (UMR-GM, Dulbecco's Modified Eagle's Medium (DMEM) containing 10% Fetal Bovine Serum, 1% Pen-Strep (10 k units Penicillin—10 k ug/mL Streptomycin) and 1% L-glutamine) in 75-150 cm² tissue culture flasks until ready for use. Cells are split at a ratio between 1:4 and 1:20 when growth reaches ≥70% confluence for routing culture maintenance. Prior to initiating an assay, cells are plated in sub-culturing flasks (25 cm² to 150 cm²) at a density of $10^6$ cells/5 cm² (example 5e6 cells for T-75). The following day, flasks are starved with assay medium (UMR-Am, Phenol Red-Free DMEM, containing 1% Bovine Serum Albumin). The following day validation samples and antibody controls are pre-incubated with PTHrP for a minimum of 30 minutes. The validation samples and controls are adjusted such that the final assay concentration of serum is equal to the assay minimum required dilution of 1:4. Twenty microliters of samples and/or controls are placed on a MSD cAMP assay plate. The starved UMR-106 cells are harvested by trypsinization and resuspended at 106 cells/mL in assay medium containing 133.5 uM of 4-(3-Butoxy-4-methoxybenzyl)-2-imidazolidinone, a cell-permeable cAMP-specific phosphodiesterase inhibitor (RO 20-1724, MW 278.35, R&D Systems/Tocris Catalog 0415). Forty microliters of the cell suspension are added to the cAMP assay plate. After a minimum of 30 minutes at room temperature with shaking, TAG cAMP detection reagent (Mesoscale Delivery, MSD Multi-Array 96-well cAMP Kit) diluted 1:200 in MSD Lysis Buffer is added to the assay plates. Plates are incubated at room temperature for an additional 1 to 2 hours with shaking. One hundred microliters of 2×MSD Read Buffer T are then added to the plates and plates are read immediately on an MSD 6000 or S6000 Sector Imager.

Results

PTHrP Drug Concentration

Relative light units (RLU) were read from assay plates on a Meso Scale Discovery (MSD) Sector 6000 electrochemiluminescent reader. Data were exported from the MSD database to permit further analysis. Calculations for establishing the assay cut point, including removal of outliers, was performed in JMP® software v12.01 (SAS, Cary, N.C.). Outlier determination proceeded stepwise. During stepwise outlier discrimination, the standard configuration of the JMP whisker and box plot was used to declare outliers. Specifically, replicates outside of whiskers (the interquartile range of the replicates (IQR) plus or minus 1.5 times the IQR) were determined to be outliers.

A drug spike assay concentration of 600 pg/mL was established during the development and qualification of the assay in human serum. FIG. 2 shows a curve fit from a single qualification run and is representative of the PTHrP dose response observed. The dotted lines indicate the EC20 and EC30 of the PTHrP response. The rounded concentrations interpolated were 436 and 728 pg/mL, respectively for the EC30 and the EC20.

Sensitivity

To evaluate sensitivity, an ultrahigh positive control sample was prepared by spiking the SPC [68.98 µg/mL] into matrix at a 1:16 dilution (4×) then serially diluting 2-fold, resulting in concentrations of the SPC of 4311, 2156, 1078, 539, 270, 135, 67 and 34 ng/mL in the assay. The dilution samples were evaluated with the assay positive controls at the MRD of 1:4 and in the presence of 600 pg/mL of PTHrP. The sensitivity was determined as the lowest concentration of the antibody dilution curve that was consistently detected as positive based on the mean RLU value, after adjusting for the MRD. Results are shown in Table 8. Antibody Sensitivity for this assay was determined to be an antibody dilution of 1:64 and both of the prepared low positive controls are likely to be below detection.

TABLE 8

Antibody Sensitivity

| 4X MRD SPC Dilution | SPC Conc. ng/mL | Run #1 Plate Cutpoint: 5841.6 | | Run #2 Plate Cutpoint: 5790.2 | | Run #3 Plate Cutpoint: 5787.1 | |
|---|---|---|---|---|---|---|---|
| | | Mean RLU | Results | Mean RLU | Results | Mean RLU | Results |
| 1:16 | 4311 | 12455 | Positive | 13842.5 | Positive | 9738 | Positive |
| 1:32 | 2156 | 9010 | Positive | 8489.5 | Positive | 5764.5 | Negative |
| 1:64 | 1078 | 6133 | Positive | 5955 | Positive | 5031.5 | Negative |
| 1:128 | 539 | 4819 | Negative | 4304 | Negative | 3833 | Negative |
| 1:256 | 270 | 4394 | Negative | 4290 | Negative | 3371.5 | Negative |
| 1:512 | 135 | 3920.5 | Negative | 3506 | Negative | 3043 | Negative |
| 1:1024 | 67 | 4206 | Negative | 3695 | Negative | 3072.5 | Negative |
| 1:2048 | 34 | 3985.5 | Negative | 3782 | Negative | 3142 | Negative |

Final Sensitivity was calculated based on the assay MRD of 4-fold.
Results are based on the mean of 2 replicates relative to the corresponding assay plate cutpoints shown.

TABLE 9

Specificity Results

| Condition | RLU | Mean RLU | St. Dev. | CV(%) | Results RLU Mean > CP = Positive | Cutpoint |
|---|---|---|---|---|---|---|
| IgG 10 µg/mL | 4253 | 3990.5 | 371.2 | 9.3 | Negative | 5378.7 |
| | 3728 | | | | | |
| *IgG 1.0 µg/mL | 17200 | 16273.5 | 1310.3 | 8.1 | Positive | |
| | 15347 | | | | | |
| IgG 0.1 µg/mL | 3726 | 3743.5 | 24.7 | 0.7 | Negative | |
| | 3761 | | | | | |

*High signal is atypical, the average HPC RLU was 7697.8

Specificity by Non-Specific Immunoglobulin

Specificity was assessed by evaluating the reactivity of commercial human IgG in the assay. Three human IgG concentrations 10, 1.0 and 0.1 pg/mL were spiked into neat human serum pool (PHS) and evaluated in the presence of a final concentration of 500 pg/mL PTH. All specificity samples were below the assay cut point of 1.234 and were considered negative. Both the 1.0 and 0.1 pg/mL samples were within the acceptance criteria of 30% of the negative control, the IgG 10 pg/mL was 60% (40% less than negative control); however, there was no impact as the sample tested negative in the assay and a negative result qualitatively demonstrates that the sample had no activity in the assay. The results are summarized in Table 4.

Specificity was performed by evaluating the reactivity of commercial human IgG in the assay. Three human IgG concentrations; 10, 1.0 and 0.1 pg/mL were spiked into human serum pool (NC) and evaluated in the presence of 600 pg/mL PTHrP. Human serum pool (NC) was spiked with 600 pg/mL PTHrP, but no IgG, to serve as the baseline control for this assay. Specificity samples with the highest and lowest IgG content were below the plate cut point of 5378.7 and were considered negative. The results are summarized in Table 9. The mid-IgG content sample 1.0 pg/mL had an atypically high signal of 16,273.5 whereas the average HPC signal in this run was only 7697.8

Specificity by Drug Tolerance

Assay specificity is such that increasing the PTHrP concentration results in a rapid decrease in signal in the presence of the SPC. Because the assay cut point is established at cellular response that is dependent upon a fixed concentration of PTHrP, it is expected that the assay will have limited drug tolerance. To evaluate this limit, the HPC, LPC1 and LPC2 were treated on individual assay plates with 900, 1200 or 2400 pg/mL of PTHrP and compared to samples treated with nominal PTHrP at 600 pg/mL.

As expected, the signal response decreased for each control with increased drug concentration. The HPC control remained positive in the presence of up to 600 pg/mL of PTHrP. As seen in section 14.5 on assay sensitivity, the LPC1 and LPC2 controls did not test positive in the nominal concentration of 600 pg/mL of PTHrP.

The presence of PTHrP in serum samples at levels above the assay concentration of 600 pg/mL may negatively impact the ability of the assay to detect neutralizing antibodies.

Selectivity

Selectivity was assessed in 10 individual placebo human serum samples. Each sample was tested unspiked as well as spiked with the SPC stock at the HPC and LPC1 dilution levels of 1:30 and 1:125 respectively and evaluated in the assay with controls at the MRD of 1:4. Samples were positive for the NAb when spiked with concentrations of antibody equal to the level of the HPC. Only two of the ten samples tested positive for NAb when spike with concentrations of antibody equal to the level of the low positive control. Three samples tested positive for NAb in the absence of antibody spike.

A reference control (NC, HPC and LPC1) was run on each assay plate for determination of the % Recovery. The % Recovery was calculated by dividing the RLU value of the 0, 1:30 or 1:125 SPC dilution spiked sample by the normalized value of the NC, HPC or LPC1, respectively and expressed as a percentage. All samples spiked at the HPC concentration of NAb were within 30% of the RLU value of their respective controls. The LPC1 control in Run 6 did not test positive in the assay.

Example 3. Determination of Anti-PTH and Anti-PTHrP Concentration

Anti-PTH or anti-PTHrP IgG concentration was determined in two rabbit polyclonal antibody reagents.

Reagents and Materials:
Greiner bio-one high binding microplate 96-well, prod #655061, L/N E16093KS
Anti-PTH (Ab)(1-34)(Human)—Phoenix Pharmaceuticals, cat #G-055-08, L/N 01553-4.
Anti-PTHrP (Ab)(1-34)(Human, Rat, Mouse)—Phoenix Pharmaceuticals, cat #H056-04, L/N 01736-1.
PTH (1-34)(Human) peptide—Phoenix Pharmaceuticals cat #055-03, L/N 430926
PTHrP (1-34)(Human, Rat, Mouse) peptide—Phoenix Pharmaceuticals cat #05604, L/N 432088
Rabbit IgG biotin—Rockland, cat #011-0602, L/N 36734
Donkey anti-Rabbit IgG (H+L) HRP, prod #711-035-152, L/N 125015
Wash buffer: 1×PBS+0.05% tween 20 (Fisher, L/N 160170) Covance in-house buffer L/N 170320-1, Exp: 17 Sep. 2017
Assay diluent: 1×PBS+3% BSA (USB/Affymetrix, prod. 10857, L/N 4295530, Exp August 2021) Covance in-house buffer L/N 170317-3, Exp: 17 Sep. 2017
Standard: Rabbit IgG whole molecule bioton conjugated, Rockland, prod #011-0602, L/N 36734, Exp: March 2018
Detecting Antibody: Donkey anti-Rabbit IgG (H+L) peroxidase conjugated, Jackson ImmunoResearch-cat #711-035-152, lot #129517, Exp: 11 Jan. 2018
ABTS peroxidase substrate (1-component)—KPL, prod #50-66-01, lot #150405, Exp: November 2017

Methods

ELISA plates (Greiner bio-one high binding microplate 96-well, prod #655061, L/N E16093KS) were coated with either PTH or PTHrP peptide solution (1 ug/mL) at a volume of 100 uL/well in assay coating buffer (PBS). Three columns of each plate were coated with various concentrations of biotin labeled rabbit IgG at a volume of 100 uL/well for the standard curve. Plates were incubated overnight at 2-8° C. After washing the plates with wash buffer (1×PBS+0.05% Tween 20), 200 uL of the blocking buffer (1×PBS+3% BSA from USB/Affymetrix Prod 10857) was added to each well and incubated at room temperature for 1 hour. Plates were washed with wash buffer (1×PBS+0.05% Tween 20) and anti-PTH or anti-PTHrP antibody samples were added to their designated wells at a volume of 50 uL per well using 2-fold serial dilutions. Diluent was added in the three columns used for developing the IgG standard curve. Plates were incubated at 35-37° C. for 1 hour. Plates were washed with wash buffer (1×PBS+0.05% Tween 20) and the secondary antibody, (donkey anti-rabbit IgG (H&L), peroxidase conjugated—Jackson ImmunoResearch, #711035152, lot 125015) was added to the entire ELISA plate. The plates were incubated for approximately 1 hour at room temperature and then washed with wash buffer (1×PBS+0.05% Tween 20). Enzyme activity that was retained on the plates was measured by adding the HRP substrate ABTS (2,2'-Azinobis [3-ethylbenzothiazoline-6-sulfonic acid]-diammonium salt—KPL #506601, lot 150405) at 100 pL per well and incubated for approximately 30 minutes at room temperature. The plates were read at 415 nm, with a reference at 570 nm. The IgG concentration was derived by comparing the absorbance of the unknown with the standard curve.

Summary Methods
Plate Coating (100 uL/well):
PTH peptide (1-34) (Human), 1 mg/mL diluted to 1 ug/mL in coating buffer
PTHrP peptide (1-34) (Human, Rat, Mouse), 1 mg/mL diluted to 1 ug/mL in coating buffer
Rabbit IgG whole molecule bioton conjugated, 1 mg/mL diluted to 1, 0.333, 0.111, 0.037, 0.012, 0.004, and 0.001 ug/mL in coating buffer (columns 10-12 only).
Incubate at 2 to 8 C overnight.
Wash 3×, 350 uL/well in wash buffer (1×PBS+0.05% tween 20) using BioTek EL406
Blocking (200 uL/well):
1×PBS+3% BSA
Incubate at room temp. for 1 hour
Wash 3×, 350 uL/well in wash buffer (1×PBS+0.05% tween 20) using BioTek EL406
Sample Placement—plate 1—(50 ul/well):
Columns 1-3—PTH (1-34) (Human) purified Ab, diluted 1:1,000 then serially diluted by 2
Columns 10-12—Assay diluent blanks
Sample Placement—plate 2—(50 ul/well):
Columns 1-3—PTHrP (1-34) (Human) antibody, diluted 1:1,000 then serially diluted by 2
Columns 10-12—Assay diluent blanks
Incubate at 35-39 C for 1 hour.
Wash 6×, 350 uL/well in wash buffer (1×PBS+0.05% tween 20) using BioTek EL406
Secondary Ab (100 uL/well):
Donkey anti-Rabbit IgG (H+L) peroxidase conjugated, diluted 1:5,000 in assay diluent
Incubate at room temp. for 1 hour.
Wash 6×, 350 uL/well in wash buffer (1×PBS+0.05% tween 20) using BioTek EL406
Substrate (100 uL/well):
ABTS peroxidase substrate (1-component)
Incubate at room temp. for 30 minutes.
Read plate at 415 nm, 570 nm using BioTek Power Wave HT plate reader, S/N 259240
Data Analysis
Quantitation is derived from Beer's Law formulation of unknown/known×concentration of known×dilution of unknown
The reference point of the standard curve (known) is the point closest to the middle of the curve (peak o.d. minus blank/2). The reference point of the unknown is the data point whose absorbance is closest to the reference point of the standard.

CONCLUSIONS

Standard curves were obtained using Rabbit IgG. ELISAs were run to determine the concentration of PTH or PTHrP in two rabbit polyclonal antibody reagents. Data points were selected from each assay correlating to the linear portion of the standard curve using Gen5 software. The results are summarized in Table 10.

TABLE 10

| Reagent | Anti-PTH antibody IgG concentration (ug/mL) | Anti-PTHrP antibody IgG concentration (ug/mL) |
|---|---|---|
| Anti-PTH (Ab)(1-34)(Human) - Phoenix Pharmaceuticals, cat# G-055-08, L/N 01553-4 | 29.84 | |
| Anti-PTHrP (Ab)(1-34)(Human, Rat, Mouse) - Phoenix Pharmaceuticals, cat# H-056-04, L/N 01736-1 | | 68.98 |

The invention claimed is:

1. An in vitro method for detecting the presence of neutralizing antibodies to abaloparatide in a sample from a subject treated with abaloparatide, the method comprising: obtaining the sample from a subject; contacting the sample with a population of cells or a cell, wherein the cell or cells comprise a receptor for abaloparatide; measuring cyclic adenosine monophosphate (cAMP) levels; and detecting the presence of neutralizing antibodies indicated by reduced cAMP levels.

2. The method of claim 1, wherein the measuring cAMP levels is performed by a competitive immunoassay.

3. The method of claim 2, wherein the competitive immunoassay is an electrochemiluminescent detection method.

4. The method of claim 1, wherein the contacting step comprises incubating the cell or cells with the serum sample.

5. The method of claim 1, wherein the method further comprises preincubation of the serum sample with a predetermined amount of abaloparatide PH prior to the contacting step.

6. The method of claim 5, wherein the preincubation is for a period of at least 30 minutes.

7. The method of claim 1, wherein the cell or cells are lysed prior to the measuring step.

8. The method of claim 1, further comprising incubation of the cell or cells with a cell permeable cAMP-specific phosphodiesterase inhibitor prior to the contacting step.

9. The method of claim 8, wherein the cAMP-specific phosphodiesterase inhibitor is 4-(3-Butoxy-4-methoxybenzyl)-2-imidazolidinone.

10. The method of claim 1, wherein the measuring cAMP levels is performed using a Mesoscale Discovery Multi-Array 96-well cAMP Plate.

11. The method of claim 1, wherein the predetermined amount of abaloparatide is at least 100, 200, 300, 400, or 500 pg/mL.

12. The method of claim 1, wherein the predetermined amount of abaloparatide is about 600 pg/mL.

13. The method of claim 1, wherein the cell or cells are rat epithelial cell line UMR-106.

14. The method of claim 13, further comprising serum-starving the UMR-106 cell or cells for a period of time prior to the contacting step.

15. The method of claim 14, wherein the period of time ranges from about 4 hours to about 48 hours, about 4 hours to about 24 hours, about 4 hours to about 16 hours, about 4 hours to about 12 hours, or about 6 hours to about 12 hours.

16. The method of claim 1, wherein the sample is a human sample.

17. The method of claim 16, wherein the human sample is a human serum sample.

18. The method of claim 1, further comprising discontinuing treatment when neutralizing antibodies are detected in the serum sample.

19. A kit for carrying out the method of claim 1, comprising components required to carry out the obtaining, contacting, measuring and detecting steps and instructions for use.

20. The method of claim 1, further comprising increasing or decreasing a dosage of abaloparatide when neutralizing antibodies are detected in the sample.

* * * * *

UNITED STATES PATENT AND TRADEMARK OFFICE
CERTIFICATE OF CORRECTION

PATENT NO. : 11,255,842 B2
APPLICATION NO. : 17/369163
DATED : February 22, 2022
INVENTOR(S) : Heidi K. Chandler It is certified that error appears in the above-identified patent and that said Letters Patent is hereby corrected as shown below:

In the Claims

At Column 21, Claim 5, Line number 34, please delete the letters "PH" after the word "abaloparatide".

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*